United States Patent
Dhillon et al.

(10) Patent No.: US 10,327,906 B2
(45) Date of Patent: Jun. 25, 2019

(54) MODULAR TALAR FIXATION METHOD AND SYSTEM

(71) Applicant: Wright Medical Technology, Inc., Memphis, TN (US)

(72) Inventors: Braham K. Dhillon, Memphis, TN (US); Shawn E. McGinley, Arlington, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 15/848,934

(22) Filed: Dec. 20, 2017

(65) Prior Publication Data

US 2018/0110625 A1    Apr. 26, 2018

Related U.S. Application Data

(63) Continuation of application No. 14/835,208, filed on Aug. 25, 2015, now Pat. No. 9,877,839.

(51) Int. Cl.
*A61F 2/42* (2006.01)
*A61F 2/30* (2006.01)
*A61B 17/80* (2006.01)

(52) U.S. Cl.
CPC ........ *A61F 2/4202* (2013.01); *A61F 2/30749* (2013.01); *A61B 17/8047* (2013.01);
(Continued)

(58) Field of Classification Search
CPC .. A61F 2002/30439; A61F 2002/30512; A61F 2002/4207
See application file for complete search history.

(56) References Cited

U.S. PATENT DOCUMENTS 5,520,690 A   5/1996   Errico et al.
5,888,204 A   3/1999   Ralph et al.
(Continued)

FOREIGN PATENT DOCUMENTS

CN   101098666 A   1/2008
CN   102048600 A   5/2011
(Continued)

OTHER PUBLICATIONS

Salvation Limb Salvage System Overview, Wright Medical Technology, Inc., [Retrieved from the internet on Sep. 9, 2016] <URL: http://www.wmtemedia.com/ProductFiles/Files/PDFs/012239_EN_LR_LE.pdf> published on Jun. 30, 2015, 6 pages.
(Continued)

*Primary Examiner* — Megan Y Wolf
(74) *Attorney, Agent, or Firm* — Duane Morris LLP

(57) ABSTRACT

A talar implant system comprises a body. The body includes a bone contact surface and an articulation surface located opposite the bone contact surface. The body defines at least one angled fastener hole extending therethrough from the articulation surface to the bone contact surface along a longitudinal axis. The articulation surface is configured to mimic articulation of the talar dome. A fastener is sized and configured to be received within the at least one fastener hole at a first angle with respect to the longitudinal axis of the fastener hole. A fastener cap is sized and configured to be received within a proximal end of the at least one fastener hole. The fastener cap couples the body to the fastener.

12 Claims, 4 Drawing Sheets

(52) U.S. Cl.
CPC ............... *A61F 2002/3079* (2013.01); *A61F 2002/30405* (2013.01); *A61F 2002/30438* (2013.01); *A61F 2002/30439* (2013.01); *A61F 2002/30538* (2013.01); *A61F 2002/4207* (2013.01); *A61F 2220/0016* (2013.01)

(56) References Cited

U.S. PATENT DOCUMENTS

| | | | |
|---|---|---|---|
| 9,655,734 | B2 | 5/2017 | Smirthwaite |
| 2005/0065521 | A1* | 3/2005 | Steger .................. A61B 17/80 606/281 |
| 2007/0129808 | A1 | 6/2007 | Justin et al. |
| 2007/0142921 | A1 | 6/2007 | Lewis et al. |
| 2009/0082875 | A1 | 3/2009 | Long |
| 2009/0198341 | A1 | 8/2009 | Choi et al. |
| 2009/0210067 | A1* | 8/2009 | Meridew .................. A61F 2/34 623/22.24 |
| 2009/0248084 | A1 | 10/2009 | Hintermann |
| 2011/0218648 | A1 | 9/2011 | Younger |
| 2014/0277538 | A1 | 9/2014 | Sander |

FOREIGN PATENT DOCUMENTS

| | | |
|---|---|---|
| CN | 103598936 A | 2/2014 |
| CN | 104411272 A | 3/2015 |
| EP | 2363087 A1 | 9/2011 |
| EP | 2832321 A1 | 9/2011 |
| JP | 2006-130317 A | 5/2006 |
| JP | 2014-036746 A | 2/2014 |
| WO | 00/66011 A | 11/2000 |
| WO | 2007/103826 A2 | 9/2007 |
| WO | 2011/110916 A1 | 9/2011 |

OTHER PUBLICATIONS

Patent Examination Report No. 1 issued in connection with corresponding Australian patent application No. 2016201814, dated Sep. 9, 2016, 8 pages.

European Search Report issued in connection with corresponding European patent application No. 16161907.7, dated May 25, 2016, 7 pages.

Office Action issued for corresponding Canadian patent application No. 2,924,440, dated Feb. 23, 2017, 3 pages.

First Office Action issued for corresponding Japanese patent application No. 2016-058219, dated May 9, 2017, 4 pages.

Office Action issued for corresponding Chinese patent application No. 201610166579.8, dated Aug. 30, 2017, 5 pages.

* cited by examiner

MODULAR TALAR FIXATION METHOD AND SYSTEM

CROSS-REFERENCE TO RELATED APPLICATIONS

This application is a continuation of U.S. patent application Ser. No. 14/835,208, filed Aug. 25, 2015, now U.S. Pat. No. 9,877,839 the entirety of which is incorporated herein by reference.

BACKGROUND

An ankle joint may become severely damaged and painful due to arthritis, prior ankle surgery, bone fracture, osteoarthritis, and/or one or more additional conditions. Options for treating the injured ankle have included anti-inflammatory and pain medications, braces, physical therapy, joint arthrodesis, and total ankle replacement.

Total ankle replacement generally comprises two components—tibial implant and a talar implant. The implants comprise articulation surfaces sized and configured to mimic the range of motion of the ankle joint. For example, the talar implant may comprise an implant sized and configured to mimic the talar dome and the tibial implant may comprise an articulation surface sized and configured to mimic articulation of the tibia. An articulating component may be located between the talar implant and the tibial implant.

Installation of a total ankle replacement can include forming one or more holes or cuts in a bone. For example, a hole may be drilled through the talus and into the tibia to create a channel for inserting a tibial stem. In some installations, additional bone is removed from the talus to make space for a talar stem extending from the talar portion.

SUMMARY

In various embodiments, a talar implant system is disclosed. The talar implant system includes an implant having a body including a bone contact surface and an articulation surface located opposite the bone contact surface. The body defines at least one fastener hole extending therethrough from the articulation surface to the bone contact surface along a longitudinal axis. A fastener is sized and configured to be partially received within a distal end of the at least one fastener hole at a first angle with respect to the longitudinal axis of the fastener hole. A fastener cap is sized and configured to be received within a proximal end of the at least one fastener hole, wherein the fastener cap couples the body to the fastener.

In various embodiments, a total joint replacement system is disclosed. The total joint replacement system includes a tibial implant sized and configured to couple to a resected tibia and a talar implant sized and configured to couple to a resected talus. The talar implant includes a body having a bone contact surface and an articulation surface located opposite the bone contact surface. The body defines at least one fastener hole extending therethrough from the articulation surface to the bone contact surface along a longitudinal axis. The at least one fastener hole is sized and configured to receive a fastener therein at a first angle with respect to the longitudinal axis of the fastener hole. A fastener cap is sized and configured to be received within a proximal end of the at least one fastener hole. The fastener cap couples the body to the fastener.

In various embodiments, a talar implant is disclosed. The talar implant comprises a body including a bone contact surface and an articulation surface located opposite the bone contact surface. The body defines at least one angled fastener hole extending therethrough from the articulation surface to the bone contact surface along a longitudinal axis. The at least one angled fastener hole is sized and configured to receive a fastener therein at a first angle with respect to the longitudinal axis of the fastener hole. A fastener cap is sized and configured to be received within a proximal end of the at least one fastener hole to couple the body to the fastener.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
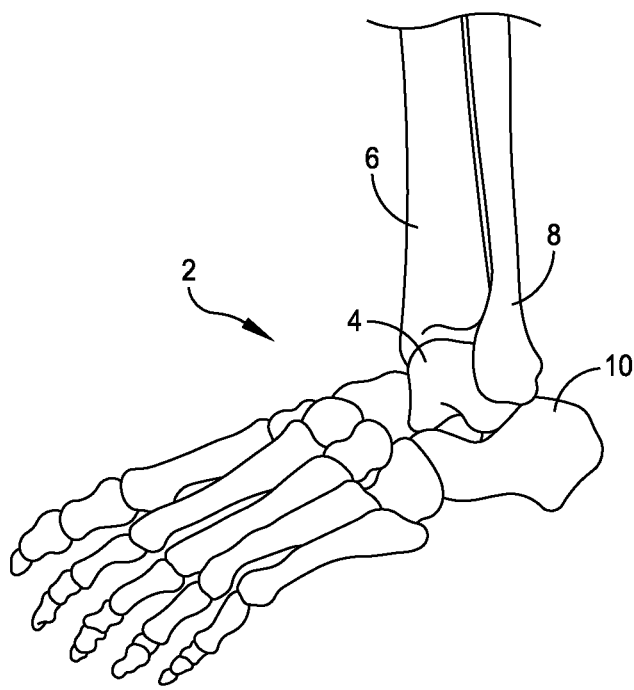
FIG. 1 illustrates an anatomic view of an ankle joint.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

In various embodiments, the present disclosure generally provides an implant for use with a total ankle replacement system. The implant includes one or more variable angle screw holes extending through the articulation surface of the implant at an angle with respect to a bone contact surface. A cap and/or retainer can be installed over the screws to couple the screws to the implant.

Figure 2:
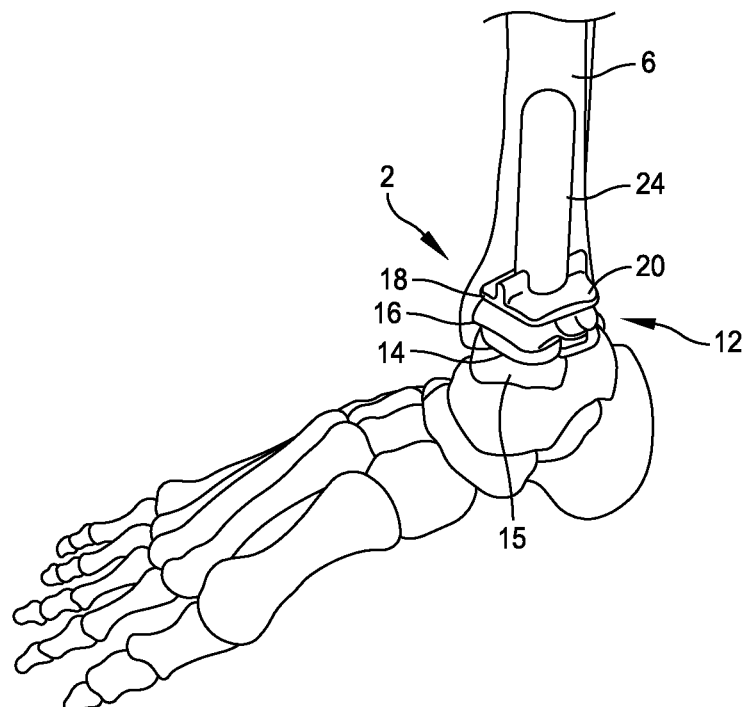
FIG. 2 illustrates one embodiment of an ankle joint having a total ankle replacement system therein.

FIG. 1 illustrates an anatomic view of an ankle joint 2. The ankle joint 2 comprises a talus 4 in contact with a tibia 6 and a fibula 8. A calcaneus 10 is located adjacent to the talus 4. In total ankle replacements, the talus 4 and the tibia 6 may be resected, or cut, to allow insertion of a talar implant and a tibial implant. FIG. 2 illustrates the ankle joint 2 of FIG. 1 having a total ankle replacement system 12 inserted therein.

The total ankle replacement system 12 comprises a talar implant 14 and a tibial implant 18. The talar implant 14 comprises a body defining a talar articulation surface 16 (or talar dome). The talar implant 14 may be anchored to the talus by one or more screws (not shown). The tibial implant 18 is sized and configured for installation into the tibia 6. The tibial implant 18 comprises a body having an articulation surface 20 and, in some embodiments, a tibial stem 24 extending into the tibia 6 to anchor the tibial implant 18. The talar joint surface 16 and the tibial joint surface 20 are mutually sized and configured to articulate. The joint surfaces 16, 20 replace the natural ankle joint surfaces, which are removed, to restore a range of motion that mimics the natural joint. One or more holes may be formed in the tibia and/or the talus prior to and during insertion of the tibial implant 18 or the talar implant 12. For example, in some embodiments, a hole is drilled starting in the bottom of the talus, extending through the talus and into the tibia. The hole may comprise, for example, a 6 mm hole configured to receive the stem 24 of the tibial implant 18.

The joint surfaces 16, 20 may be made of various materials, such as, for example, polyethylene, high molecular weight polyethylene (HMWPE), rubber, titanium, titanium alloys, chrome cobalt, surgical steel, and/or any other suitable metal, ceramic, sintered glass, artificial bone, and/or any combination thereof. The joint surfaces 16, 20 may comprise different materials. For example, the tibial joint surface 20 may comprise a plastic or other non-metallic material and the talar joint surface 16 may comprise a metal surface. Those skilled in the art will recognize that any suitable combination of materials may be used.

Figure 3:
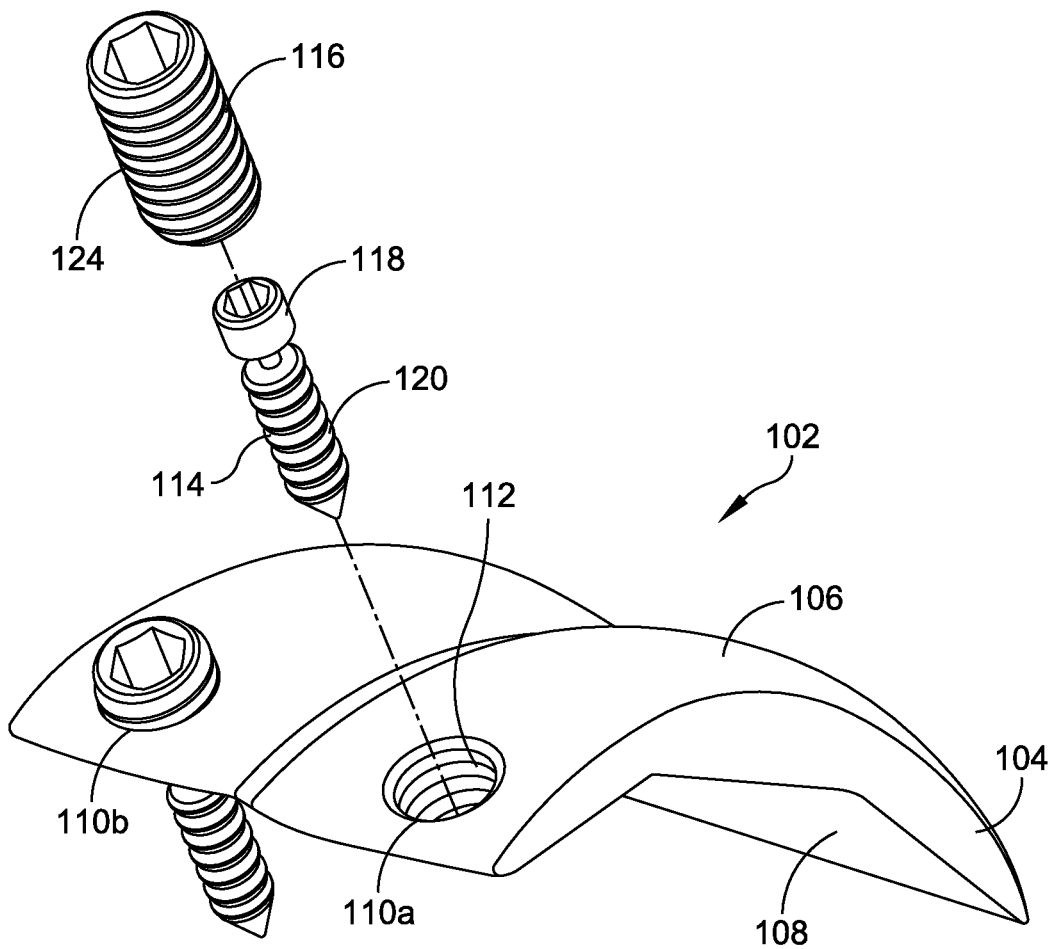
FIG. 3 illustrates one embodiment of an implant having one or more angled fastener holes formed through an articulation surface.

FIG. 3 illustrates one embodiment of an implant 102 having one or more fastener holes 110a, 110b formed through an articulation surface 106. The implant 102 comprises a body 104 having an articulation surface 106 and an opposed bone contact surface 108. The body 104 has a predetermined thickness between the articulation surface 106 and the bone contact surface 108. The predetermined thickness can be constant and/or variable. The articulation surface 106 is sized and configured to interface with an opposing joint surface of an opposing implant. For example, in one embodiment, the articulation surface 106 is sized and configured to interface with a joint surface of a tibial implant, such as, for example, the tibial implant 18 shown in FIG. 2. In another example, the articulation surface 106 is sized and configured to interface with an articulation body located between a tibial implant 18 and the talar dome 106. The bone contact surface 108 comprises a surface configured to contact a resected bone section. For example, in some embodiments, the bone contact surface 108 is configured to rest on and couple to a resected talus. In other embodiments, the bone contact surface 108 is configured to couple to a plate anchored to the bone. The bone contact surface 108 may comprise a planar surface, a concave surface, and/or any desirably shaped surface. For example, in the illustrated embodiment, the bone contact surface 108 comprises a concave surface.

In various embodiments, the implant 102 comprises one or more fastener holes 110a, 110b extending through the body 104. The fastener holes 110a, 110b extend from the articulation surface 106 through the body 104 to the bone contact surface 108. The fastener holes 110a, 110b are sized and configured to receive a fastener 114 therein. In some embodiments, the fastener 114 comprises a head 118 and a threaded section 120. The threaded section 120 is configured to couple to a bone, such as, for example, a talus and/or a plate. Although a single thread is illustrated, it will be appreciated that the fastener 114 may include any number of threads on the threaded section 120 and/or on the head 118. In various embodiments, the fastener 114 may comprise a screw (such as a bone screw, a slotted screw, and/or any other suitable screw), a peg (such as a coated and/or an uncoated peg) and/or any other suitable fastener. The fastener holes 110a, 110b may define one or more internal thread patterns 112.

The fastener holes 110a, 110b can be formed through the body 104 at any suitable angle. For example, in the illustrated embodiment, the fastener holes 110a, 110b are formed through the articulation surface 106 at an angle of about 0°, e.g., the fastener holes 110a, 110b have a longitudinal axis substantially perpendicular with a tangent line of the curve of the articulation surface 106 at a center of the fastener hole 110a, 110b. In other embodiments, the fastener holes 110a, 110b may be formed at any angle with respect to the articulation surface. For example, in various embodiments, the fastener holes 110a, 110b can include longitudinal axes positioned at any angle with respect to a tangent line of the curve of the articulation surface 106, such as, for example, an angle between 0 and 30 degrees, 0 and 45 degrees, 0 and 60 degrees, or 0 and 90 degrees. Although specific angles are given herein as examples, it will be appreciated by those skilled in the art that the fastener holes 110a, 110b may be formed in the body 104 at any angle with respect to the articulation surface 106 and/or the bone contact surface 108.

In some embodiments, the fastener 114 is sized and configured to be inserted into the fastener holes 110a, 110b at an angle with respect to a longitudinal axis of the fastener holes 110a, 110b. For example, in some embodiments, the fastener 114 may be inserted at an angle of between 0 and 90 degrees, such as, for example, 30 degrees, 45 degrees, or 60 degrees. In some embodiments, the angle between the fastener 114 and the longitudinal axis of the fastener hole 110a, 110b is predetermined. In other embodiments, the angle between the fastener 114 and the longitudinal axis of the holes 110a, 110b is variable and/or selectable within a predetermined range. A clinician may select an angle for the fastener during installation of the implant 102. Although specific angles are given herein as examples, it will be appreciated by those skilled in the art that the fasteners 114 may be inserted into the fastener holes 110a, 110b at any suitable angle with respect to the longitudinal axis of the fastener holes 110a, 110b. In some embodiments, the angles of the fasteners 114 in each of the fastener holes 110a, 110b are the same. In other embodiments, the angles of fasteners 114 in each of the angled fastener holes 110a, 110b are different.

In some embodiments, the fastener holes 110a, 110b comprise a diameter larger than the diameter of a head 118 of the fastener 114. The fasteners 114 can freely slide through the angled fastener holes 110a, 110b and do not interface with internal threads 112 of the holes 110a, 110b. The fasteners 114 can be inserted into a specific position in a bone prior to installation of the implant 102. After the fasteners 114 are positioned, the implant 102 is placed on the bone such that the fasteners 114 are located within the fastener holes 110a, 110b. In other embodiments, the fasteners 114 may be installed through the fastener holes 110a, 110b after the implant 102 is positioned on a bone. After positioning the fasteners 114 within the fastener holes 110a, 110*b*, a fastener cap 116 can be inserted into a proximal end of each of the fastener holes 110*a*, 110*b* to secure the body 104 to the fasteners 114.

Figure 7:
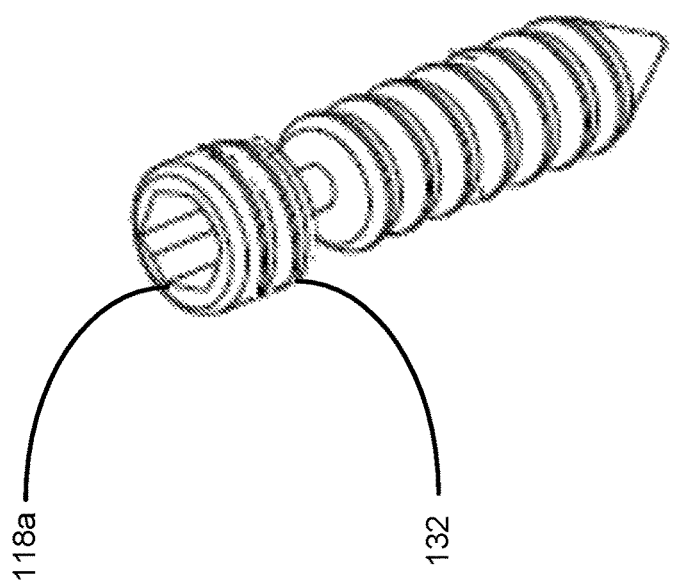
FIG. 7 illustrates a fastener having a threaded head, in accordance with some embodiments.
Figure 6:
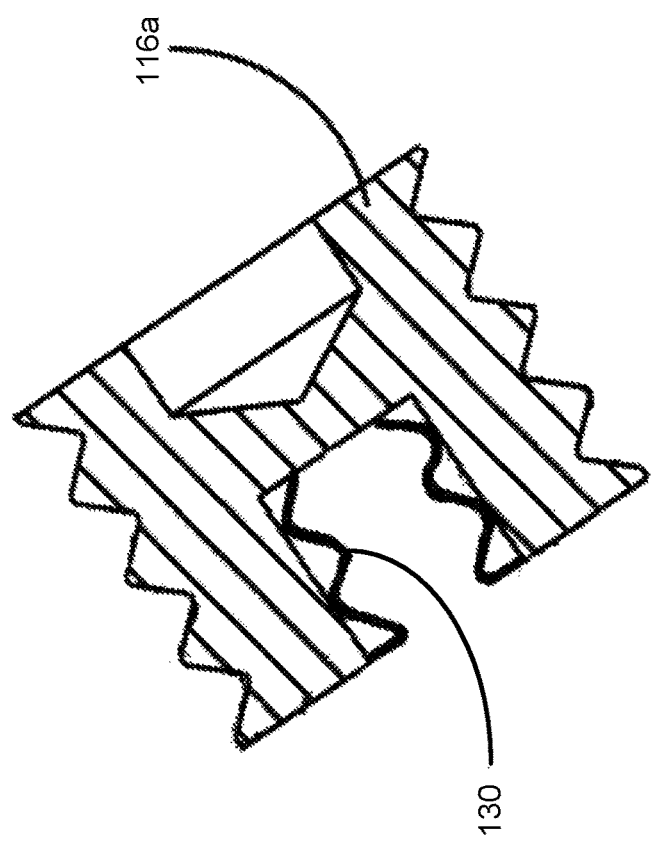
FIG. 6 illustrates a cross-sectional view of a fastener cap having an internally threaded cavity, in accordance with some embodiments.

In some embodiments, the fastener cap 116 includes external threads configured to mate with the internal threads 112 of the fastener holes 110*a*, 110*b*. The fastener cap 116 includes a blind cylindrical cavity 122 at a distal end configured to interface with a head 118 of the fastener 114. For example, in some embodiments, the fastener cap 116 acts as a set screw that maintains the implant 102 and the fastener 114 in a locked relationship. In some embodiments, as shown in FIGS. 6-7, the cavity 122 of the fastener cap 116*a* includes internal threads 130 sized and configured to couple to threads 132 formed on the head 118*a* of a fastener. The fastener cap further includes a transverse wall at a proximal closed end of the distal cavity.

In some embodiments, the fastener cap 116 is sized and configured to be flush with the articulation surface 106 when in a locked position, e.g., fully inserted into the fastener hole 110*a*, 110*b*. In some embodiments, the fastener cap 116 is sized and configured to sit below the articulation surface 106 when in a locked position. An additional articulation cap (not shown) may be inserted over the fastener cap 116 to fill the fastener hole 110*a*, 110*b* and provide a solid, smooth articulation surface 106. In some embodiments, the fastener cap 116 extends beyond the articulation surface 106 when in a locked position. The fastener cap 116 may operate as a rotational stop for an implant placed in an articulating arrangement with the articulation surface 106. For example, in some embodiments, the fastener cap 116 may operate as a rotational stop for a tibial implant in an articulating relationship with the implant 102.

Figure 4:
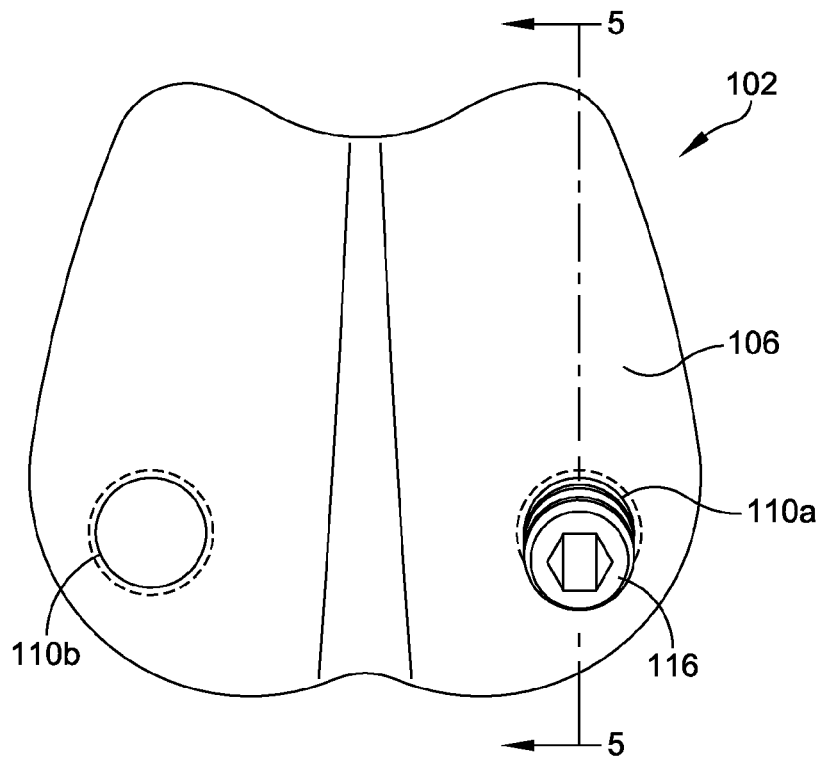
FIG. 4 illustrates a bottom-view of the implant of FIG. 3.
Figure 5:
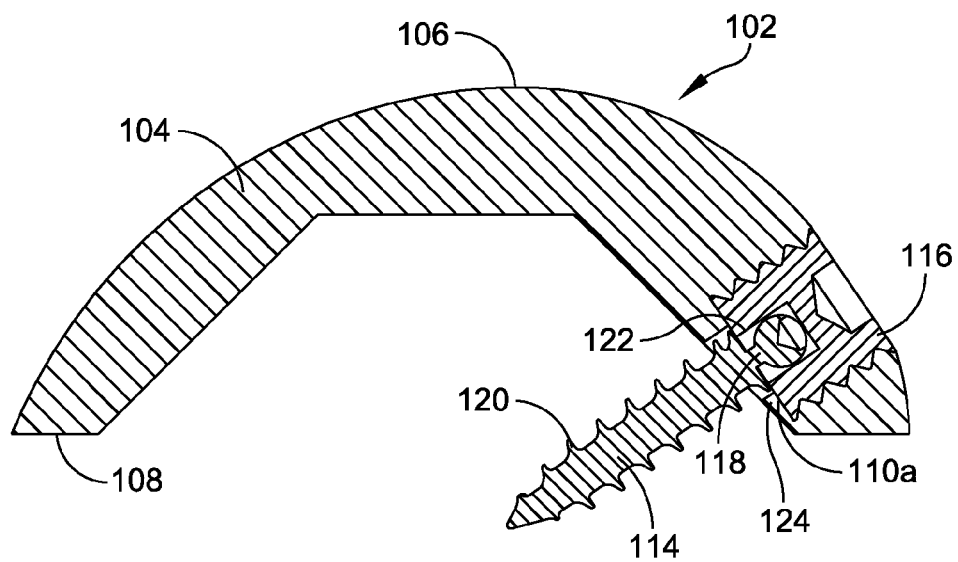
FIG. 5 illustrates a cross-sectional view of the implant of FIG. 3 taken along line 5-5 in FIG. 4.

FIG. 5 illustrates the a cross-sectional view of the implant 102 taken along line 5-5 of FIG. 4. As shown in FIG. 5, the fastener 114 has a diameter less than the internal diameter of the holes 110*a*, 110*b* such that the fastener 114 fits within the holes 110*a*, 110*b* at a variable angle without interfacing with and/or contacting the internal threads 112 of the hole 110*a*, 110*b*. A fastener cap 116 can be inserted into a proximal end of the hole 110*a*, 110*b*. The fastener cap 116 includes a distal cavity 122 sized and configured to receive a fastener head 118 therein. The fastener cap 116 locks the implant 102 to the fastener 114 such that the fastener 114 and the fastener cap 116 maintain the implant 102 in a fixed position with respect to a bone. In some embodiments, the fastener hole 110*a*, 110*b* comprises a lip 124 formed at a distal end to prevent the fastener cap 116 from being inserted beyond a predetermined depth. The distal lip 124 may correspond to a fully locked position of the fastener cap 116

In some embodiments the fastener 114 can be positioned at a predetermined angle with respect to the bone contact surface 108 of the talar dome 102. For example, in some embodiments, the fastener 114 is inserted into the bone at an angle with respect to a longitudinal axis of the fastener hole 110*a*, 110*b*. The fastener 114 may be inserted at any suitable angle with respect to the longitudinal axis of the hole 110*a*, 110*b*, such as, for example, any angle between 0 and 90 degrees, 0 and 60 degrees, 0 and 45 degrees, 0 and 30 degrees, and/or any other suitable angle. In some embodiments, the head 118 of the fastener 114 and/or the cavity 122 of the fastener cap 116 are sized and configured to allow the fastener cap 116 and the fastener 114 to interface at a variety of angles. For example, in some embodiments, the head 118 of the fastener 114 includes a rounded, or ball-type, head. The cavity 122 is a socket-type cavity configured to interface with the head 118 of the fastener 114. The ball-and-socket coupling allows the fastener 114 to be placed at a variety of angles with respect to the talar dome 102 and coupled to the talar dome 102 by the fastener cap 116. The fastener 114 may comprise any suitable fixation device, such as, for example, a screw, a peg, a coated peg, a slotted screw, a push-fit fastener, and/or any other suitable fastener.

Although the implant 102 is shown having two angled fastener holes 110*a*, 110*b* located on a first side of the articulation surface 106, it will be appreciated that the implant 102 may comprise any suitable number of fastener holes 110*a*, 110*b* such as, for example, one, two, or four fastener holes 110*a*, 110*b*. In addition, the fastener holes 110*a*, 110*b* may be located in any suitable position on the articulation surface 106, such as, for example, on the same side (as shown in FIG. 1), on opposite sides, and/or on multiple sides of the articulation surface.

In various embodiments, an implant system is disclosed. The implant system includes an implant having a body including a bone contact surface and an articulation surface located opposite the bone contact surface. The body defines at least one fastener hole extending from the articulation surface to the bone contact surface along a longitudinal axis. A fastener is sized and configured to be partially received within a distal end of the at least one fastener hole at a first angle with respect to the longitudinal axis of the fastener hole. A fastener cap is sized and configured to be received within a proximal end of the at least one fastener hole, wherein the fastener cap couples the body to the fastener.

In some embodiments, the at least one fastener hole comprises a plurality of internal threads. The fastener can have a first diameter less than a diameter of the internal threads of the fastener hole.

In some embodiments, the fastener cap includes a plurality of external threads sized and configured to couple to the internal threads of the at least one fastener hole. The fastener cap can include a distal cavity sized and configured to receive a head of the fastener therein. In some embodiments, the distal cavity comprises a socket and the head of the fastener comprises a ball. In some embodiments, the distal cavity defines a plurality of internal threads and the head of the fastener defines a plurality of external threads sized and configured to interface with the plurality of internal threads of the distal cavity. The fastener can comprise a bone screw.

In various embodiments, a total joint replacement system is disclosed. The total joint replacement system includes a tibial implant sized and configured to couple to a resected tibia and a talar implant sized and configured to couple to a resected talus. The talar implant includes a body having a bone contact surface and an articulation surface located opposite the bone contact surface. The body defines at least one fastener hole extending therethrough from the articulation surface to the bone contact surface along a longitudinal axis. The at least one fastener hole is sized and configured to receive a fastener therein at a first angle with respect to the longitudinal axis of the fastener hole. A fastener cap is sized and configured to be received within a proximal end of the at least one fastener hole. The fastener cap couples the body to the fastener.

In some embodiments, the at least one fastener hole comprises a plurality of internal threads. The fastener can have a first diameter less than a diameter of the internal threads of the fastener hole. In some embodiments, the fastener cap includes a plurality of external threads sized and configured to couple to the internal threads of the at least one fastener hole. The fastener cap can include a distal cavity sized and can be configured to receive a head of the fastener therein. In some embodiments, the distal cavity comprises a socket and the head of the fastener comprises a ball. In some embodiments, the distal cavity defines a plurality of internal threads and the head of the fastener defines a plurality of external threads sized and configured to interface with the plurality of internal threads of the distal cavity. The fastener can comprise a bone screw.

In various embodiments, a talar implant is disclosed. The talar implant comprises a body including a bone contact surface and an articulation surface located opposite the bone contact surface. The body defines at least one angled fastener hole extending therethrough from the articulation surface to the bone contact surface along a longitudinal axis. The at least one angled fastener hole is sized and configured to receive a fastener therein at a first angle with respect to the longitudinal axis of the fastener hole. A fastener cap is sized and configured to be received within a proximal end of the at least one fastener hole to couple the body to the fastener.

In some embodiments, the at least one fastener hole comprises a plurality of internal threads. The fastener can have a first diameter less than a diameter of the internal threads of the fastener hole. The fastener cap can comprise a plurality of external threads sized and configured to couple to the internal threads of the at least one fastener hole.

Although the subject matter has been described in terms of exemplary embodiments, it is not limited thereto. Rather, the appended claims should be construed broadly, to include other variants and embodiments, which may be made by those skilled in the art.

What is claimed is:

1. A talar implant system comprising:
   an implant having a bone contact surface and an articulation surface located opposite the bone contact surface, the implant defining a fastener hole extending from the articulation surface to the bone contact surface along a longitudinal axis, the fastener hole having internal threads;
   a fastener sized and configured to be partially received within a distal end of the fastener hole, the fastener having a head; and
   a fastener cap having external threads configured to engage the internal threads of the fastener hole, the fastener cap including a distal cavity sized and configured to receive the head of the fastener to couple the implant to the fastener, wherein the distal cavity is a blind cylindrical cavity, and wherein the fastener cap is configured to be inserted into a proximal end of the fastener hole after the head of the fastener is partially received within the distal end of the fastener hole.

2. The talar implant system of claim 1, wherein the distal cavity of the fastener cap includes internal threads and the head of the fastener includes external threads configured to engage the internal threads of the cavity.

3. The talar implant system of claim 1, wherein the head of the fastener comprises a ball.

4. The talar implant system of claim 1, wherein the fastener comprises a bone screw.

5. The talar implant system of claim 1, wherein the fastener cap includes a transverse wall at a proximal end of the distal cavity.

6. The talar implant system of claim 1, wherein a maximum diameter of the fastener is less than a diameter of the internal threads of the fastener hole.

7. A talar implant system comprising:
   an implant having a bone contact surface and an articulation surface located opposite the bone contact surface, the implant defining a fastener hole extending from the articulation surface to the bone contact surface along a longitudinal axis;
   a fastener sized and configured to be partially received within a distal end of the fastener hole, the fastener having a head; and
   a fastener cap configured to be received in the fastener hole of the implant, the fastener cap including a distal cavity sized and configured to receive the head of the fastener to couple the implant to the fastener and a transverse wall at a proximal closed end of the distal cavity, wherein the distal cavity is cylindrical, and wherein the fastener cap is configured to be inserted into a proximal end of the fastener hole after the head of the fastener is partially received within the distal end of the fastener hole.

8. The talar implant system of claim 7, wherein the head of the fastener comprises a ball.

9. The talar implant system of claim 7, wherein the fastener comprises a bone screw.

10. The talar implant system of claim 7, wherein the distal cavity of the fastener cap includes internal threads and the head of the fastener includes external threads configured to engage the internal threads of the cavity.

11. The talar implant system of claim 10, wherein the fastener hole includes internal threads and the fastener cap includes external threads configured to engage the internal threads of the fastener hole.

12. The talar implant system of claim 11, wherein a maximum diameter of the fastener is less than a diameter of the internal threads of the fastener hole.

* * * * *